US00PP34802P2

(12) United States Plant Patent

Schatz et al.

(10) Patent No.: US PP34,802 P2
(45) Date of Patent: Dec. 6, 2022

(54) *CANNABIS* PLANT NAMED 'UNIQUE FLOWER ORIGINAL HAZE'

(50) Latin Name: *Cannabis sativa*
Varietal Denomination: UNIQUE FLOWER ORIGINAL HAZE

(71) Applicant: Unique Flower LLC, Rainier, OR (US)

(72) Inventors: Daniel Schatz, Rainier, OR (US); Nicole Schatz, Rainier, OR (US)

(73) Assignee: Unique Flower LLC, Rainier, OR (US)

( * ) Notice: Subject to any disclaimer, the term of this patent is extended or adjusted under 35 U.S.C. 154(b) by 0 days.

(21) Appl. No.: 17/553,744

(22) Filed: Dec. 16, 2021

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258
See application file for complete search history.

(56) References Cited

PUBLICATIONS https://www.icmag.com/forum/marijuana-growing/cannabis-flower-photos/123914-original-haze (Retrieved from the Internet on Mar. 28, 2022.).*
https://leafmagazines.com/learn/behind-the-strain-original-haze/ (Retrieved from the Internet on Mar. 28, 2022).*
Guzman-Gutierrez, S.L., et al., Linalool and -pinene exert their antidepressant-like activity through the monoaminergic pathway, Life Sciences, 2015, 128:24-29.
Ahn, K., et al., Fatty acid amide hydrolase as a potential therapeutic target for the treatment of pain and CNS disorders, Expert Opin. Drug. Discov., 2009, 4(7):763-784.
Hirota, R., et al., Limonene inhalation reduces allergic airway inflammation in Dermatophagoides farinae-treated mice, Inhalation Toxicology, 2012, 24(6):373-381.
Hands, L.O., et al., Terpenes in Cannanbis: Are they Important?, Med Cannabis Cannabinoids, 2020, 3:25-60, Karger, online.
Jansen, C., et al., Myrcene and terpene regulation of TRPV1, Channels, 2019, 13:1, 344-366, Taylor and Francise online.
Scherma, M., et al., Brain activity of anandamide: a rewarding bliss?, Acta Pharmacologica Sinica, 2019, 40:309-323, National Library of Medicine, onine.
Rufino, A.T., et al..Evaluation of the anti-inflammatory, anti-catabolic and pro-anabolic effects of E-caryophyllene, myrcene and limon, European J. Pharm., 2015, 750:141-150.
Cascone, P., et al., J., Tobacco overexpressing -ocimene induces direct and indirect responses against aphids in receiver tomato plants, Plant Physiology, 2015, 173:28-32.
Wojtunik-Kulesza, K. A., et al., Volatile terpenoids as potential drug leads in Alzheimer's disease, Open Chem, 2017, 15:332-343, De Gruyter Open Access.

* cited by examiner

*Primary Examiner* — Susan McCormick Ewoldt
(74) *Attorney, Agent, or Firm* — Squire Patton Boggs LLC (US)

(57) ABSTRACT

The present invention provides a new and distinct *Cannabis sativa* cultivar designated as 'UNIQUE FLOWER ORIGINAL HAZE'. This new cultivar is characterized by a persistent green phenotype, extreme resin production, flowering at 14-16 weeks, and significant resistance to pests and fungal growth. 'UNIQUE FLOWER ORIGINAL HAZE' is characterized by high levels of Myrcene and Ocimene 2, moderate levels of cis-β Farnesene and β Caryophyllene, and lower levels of additional terpenes including pinenes, α-humulene, linalool, and limonine. 'UNIQUE FLOWER ORIGINAL HAZE' has on average 17.38% Total THC and 0.1% Total CBD by dry weight.

10 Drawing Sheets

Latin name of the genus and species of the plant claimed:
Latin name of genus and species: *Cannabis sativa.*
Variety denomination: 'UNIQUE FLOWER ORIGINAL HAZE'.

BACKGROUND OF THE INVENTION

The present invention relates to a new and distinct cultivar of *Cannabis sativa*, ssp. *sativa*, hereinafter referred to by the cultivar name 'UNIQUE FLOWER ORIGINAL HAZE'.

This new cultivar was identified at facilities in Rainier, Oreg., among plants derived from crosses of the progeny of three historic Columbian landrace varieties, namely, Punto Rojo, Highland Columbian Gold, and Santa Marta Columbian Gold.

Punto Rojo (Not Patented), also known as Red Dot, was grown in the lowlands of Columbia and recognized by its namesake red dots or coloration on calyxes (bracts) of dense floral clusters that appeared on most phenotypic expressions as well as the red striping or coloration of the stalk. It could be very tall (up to 3 m in height). Punto Rojo was known to provide a very heavy and intense body high and introspective/loopy cerebral effects. The terpene profile included aromas of woods, sandalwood, cedar, black pepper, metal, and incense. Tests of plants believed to be similar to the original race had total THC of 13-18%, total CBD of 0.32-0.96%, myrcene of 0.39% and ocimene of 0.22%.

Highland Columbian Gold (Not Patented) was grown in the highlands of Columbia and included phenotypes that expressed gold floral clusters as well as phenotypes that were green. Highland Columbian Gold grew into tall (>2.3 m), lanky plants with no coloration on the stem and wispy floral clusters. Highland Columbian Gold was known to provide a soaring, uplifting, long-lasting high. The terpene profile included aromas of ginger, sassafras, frankincense, incense, pine, wood, sandalwood, and herbs. Tests of plants believed to be similar to the original race had total THC of 18-19.5%, total CBD of 0.25-0.5%, myrcene of 0.15% and ocimene of 0.03%.

Santa Marta Columbian Gold (Not Patented) was also a highland variety, characterized by fluffy and crystal-covered buds that could be gold or green. It had a shorter (1.5-2 m) plant structure than Highland Columbian Gold and no coloration on the stems. It was known to provide a profound, trippy, mellow, and spacious effect. The terpene profile included aromas of woods, pine, sandalwood, and black pepper. Tests of plants believed to be similar to the original race had total THC of 22-25% and total CBD of 0.79-1.23%.

Plants from each of these three "narrow-leaved" landraces were allowed to grow and open-pollinate in the field in the locality of Santa Cruz, Calif. over many generations. Unlike many common strains of *Cannabis*, these plants were not domesticated or bred for commercial purposes (Robert C. Clarke & Mark D. Merlin (2016) *Cannabis* Domestication, Breeding History, Present-day Genetic Diversity, and Future Prospects, Critical Reviews in Plant Sciences, 35:5-6, 293-327). More recently, their progeny were grown indoors in Rainier, Oreg., and they expressed a number of different phenotypes, including silver, silver blue, purple, gold, and lime green phenotypes. Each of these phenotypes expressed other different traits, including different cannabinoid and terpene profiles, colorations, and structure.

The plant designated as 'UNIQUE FLOWER ORIGINAL HAZE' was identified by the inventors on the basis of its green floral phenotype, which does not change color on the calyx regardless of temperatures, and which is associated with a unique chemotype that provides distinctive effects when used by humans. The plant is relatively short (1.6-1.9 m) and has red striping on its stems. The plant also exhibits favorable resin production, yield, and pest and disease resistance. The combination of traits from the distinctive ancestral land race population came together to create an altogether unique new cultivar. The mix of parental floral structure lead to the unique open bud, foxtail structure of 'UNIQUE FLOWER ORIGINAL HAZE'. Unlike its parental plants that were known for their coloration, 'UNIQUE FLOWER ORIGINAL HAZE' does not express color on the calyxes or floral clusters. 'UNIQUE FLOWER ORIGINAL HAZE' expresses vegetative growth traits that lean towards the wispy floral clusters and lanky growth pattern of Highland Columbian Gold, with stem coloration from Punto Rojo. The total THC is similar to existing Punto Rojo plants and lower than existing Columbian Gold plants. However, the full chemotype of UNIQUE FLOWER ORIGINAL HAZE is unique, being characterized by very low total CBD (0.1%), high ocimene (0.51%), and very high myrcene (0.84%).

BRIEF SUMMARY OF THE INVENTION

The novel plant disclosed herein was selected for its combination of traits unique to this individual plant, including its distinctive chemotype characterized by high THC, low CBD, high ocimene, and very high myrcene with low levels of complementary terpenes, in combination with other features providing high productivity and hardiness.

More specifically, 'UNIQUE FLOWER ORIGINAL HAZE' has on average 17.38% Total THC and 0.10% Total CBD by dry weight, and 8.4 mg/g of β-Myrcene and 5.1 mg/g of Ocimene 2. 'UNIQUE FLOWER ORIGINAL HAZE' has relatively moderate levels of the terpenes cis-β-Farnesene and β-Caryophyllene, with additional terpenes, including α-Pinene, Limonene, Humulene and Linalool, occurring at lower levels. The chemical profile of 'UNIQUE FLOWER ORIGINAL HAZE' is believed to provide its unique effects, including positivity of thought and stimulation of mental function together with soothing and calming effects on the body, which may have anti-depressant effects and reduce neuropathic dysfunction (e.g. PTSD, anxiety), particularly in etiologies involving inflammation. Until now research has indicated that *Cannabis* having a myrcene content equal to or greater than 0.5% will produce a heavy, narcotic effect known as "couchlock" (Hanus, L. O., et al., Med *Cannabis* Cannabinoids, 3:25-60 (2020); www.karger.com/Article/FullText/509733; Piomelli, D., et al., *Cannabis* and Cannabinoid Research, 1.1: 44 (2016); www.liebertpub.com/doi/10.1089/can.2015.29003.ebr). Remarkably, this is not the case with 'UNIQUE FLOWER ORIGINAL HAZE'.

The plant designated as 'UNIQUE FLOWER ORIGINAL HAZE' has a relatively long growing period, like its ancestral populations, with 14-16 weeks to harvest. Long-flowering "Narrow Leaf Drug" (NLD) varieties of *Cannabis* derived only from the Columbian landraces are rare in today's commercial *Cannabis* industry, in part because historic prohibition of *Cannabis* favored selection and development of fast-flowering varieties that could be harvested before detection by authorities. The NLD varieties were hybridized with the faster flowering Wide Leaf Drug (WLD) varieties, mostly hash plants from the Middle East, and were then selected and bred towards the WLD variety side, with faster flowering, denser floral formations, and high THC/CBD chemotype without regard to terpene profile. 'UNIQUE FLOWER ORIGINAL HAZE' preserves the long flowering period characteristic of its ancestral populations, and certain other features such as narrow leaves, looser floral formations and a laxly branched growth form. Unlike the ancestral populations from which it was derived, 'UNIQUE FLOWER ORIGINAL HAZE' has high THC. It is also very hardy, being resistant to pests and diseases, and is very productive, having dense glandular trichomes and extreme resin production, unlike other progeny of these ancestral land race plants. 'UNIQUE FLOWER ORIGINAL HAZE' is also distinguishable from progeny of these ancestral landrace plants by its terpene profile including, in particular, its very high levels of myrcene and ocimene. In this regard, 'UNIQUE FLOWER ORIGINAL HAZE' is also unlike WLD varieties on the market today, which have even higher levels of THC and markedly lower levels of myrcene, if any. Thus, 'UNIQUE FLOWER ORIGINAL HAZE' is not only unique among commercial *Cannabis*, it is different from its ancestral populations and unique among the progeny of the relatively rare Columbian landraces that have not undergone hybridization with WLD varieties.

This new cultivar was asexually reproduced via stem-cutting and cloning using two different methods. In the first, lateral shoots were cut at an internode leaving a 4-6" cutting that was then dipped into a rooting hormone, inserted into a Rapid Tooter plant starter cube, and placed into a clone dome for 8-14 days or until roots were visible. In the second, cuttings were taken and placed in plain water for at least 24 hours, then transplanted straight into soil. Both methods were performed by the inventors at the Unique Flower LLC facilities in Rainier, Oreg., with asexual clones grown in greenhouses at the facilities in Rainier, Oreg. The stem cuttings resulting in asexual propagation were approximately 14 cm long and had multiple auxiliary meristems. These clones were allowed to root for 14 to 18 days prior to being introduced to large raised beds. They were lightly fed with organic inputs, and defoliated and pruned as necessary throughout their growing cycle. The clones were flowered in a light deprivation greenhouse with 315 Ceramic Metal Halides as supplemental lighting. The floral transition was initiated by switching to 11 hour days and 13 hour nights in the greenhouse. Flowering continued for 14-15 weeks until harvest, at which point morphological measurements were taken, samples were taken for chemical analysis, and yield was quantified.

The unique and desirable properties of 'UNIQUE FLOWER ORIGINAL HAZE', including (but not limited to) those identified in the Table 1 and discussed in more detail herein, were found to be transmissible by this asexual reproduction in greenhouses at 2971 Zimmerman Rd. in Rainier, Oreg. The asexually reproduced plants also maintained the sexual stability of the mother plant.

TABLE 1

Key properties.

| Property | 'UNIQUE FLOWER ORIGINAL HAZE' |
|---|---|
| Total THC | 17.38% |
| Total CBD | 0.1% |
| β-Myrcene | 0.84% |
| Ocimene 2 | 0.51% |
| B-Caryophyllene | 0.20% |
| α-Pinene | 0.12% |
| α-Humulene | 0.09% |
| Linalool | 0.06% |
| Limonene | 0.04% |
| Aroma | Fresh/sharp vegetable and herbs, pepper, grains of paradise |
| Psychoactive Effects | Euphoric, thought provoking, mind expanding, uplifting |
| Physiological Effects | Calming |
| Pest Resistance | High |
| Disease Resistance | High |
| Resin Production | Extremely high |

BRIEF DESCRIPTION OF THE DRAWINGS

The accompanying color photographs depict characteristics of 'UNIQUE FLOWER ORIGINAL HAZE'. The colors shown are as true as can be reasonably obtained by digital photographic procedures and have not been enhanced or adjusted in any way.

CHEMICAL CONSTITUENTS

Figure 1:
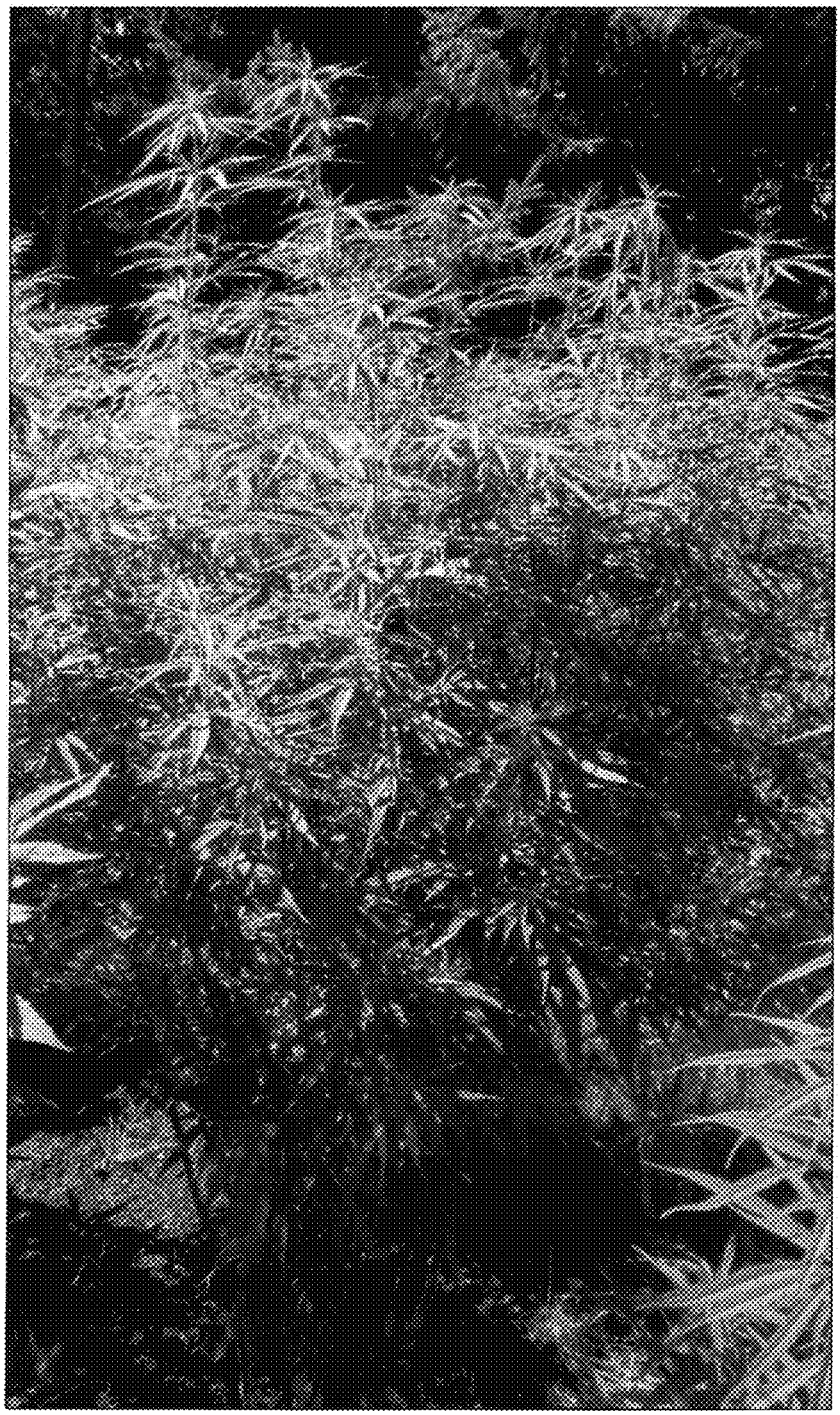
FIG. 1 shows the growth form of 'UNIQUE FLOWER ORIGINAL HAZE' after transplantation from the greenhouse to a field plot at facilities in Rainier, Oreg.
Figure 2:
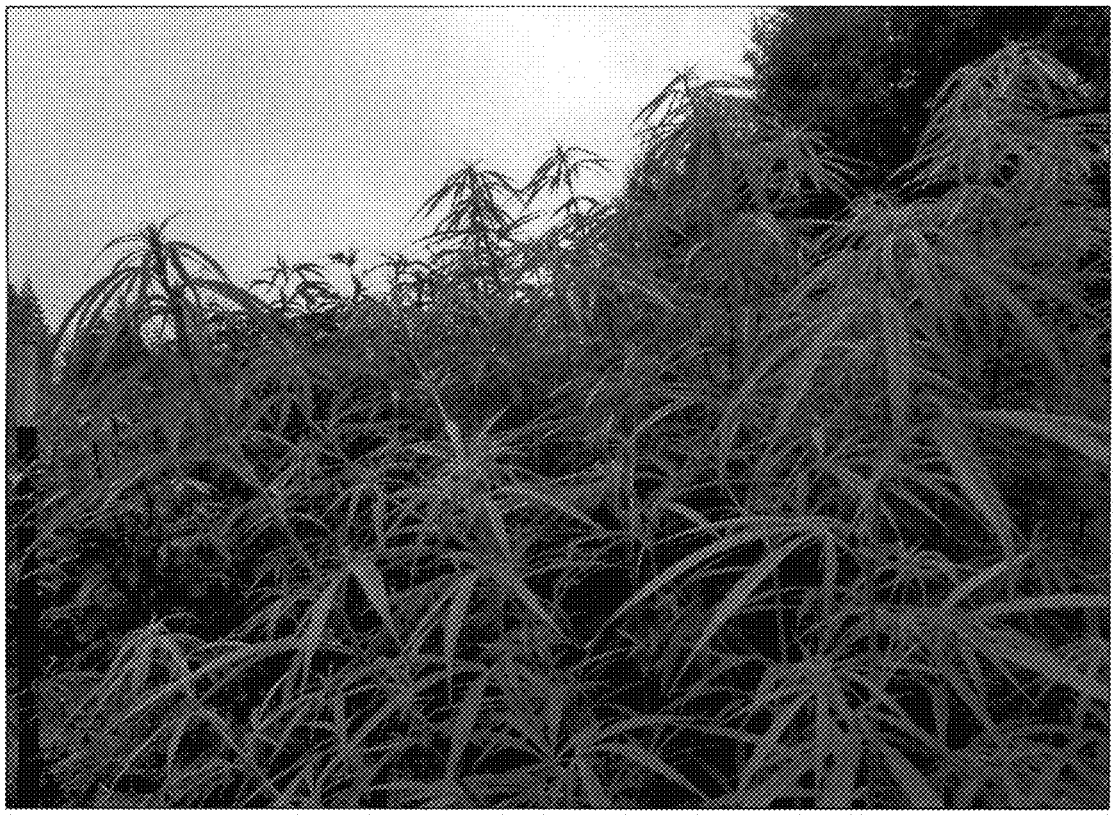
FIG. 2 shows stem and leaf structure of 'UNIQUE FLOWER ORIGINAL HAZE'.
Figure 3:
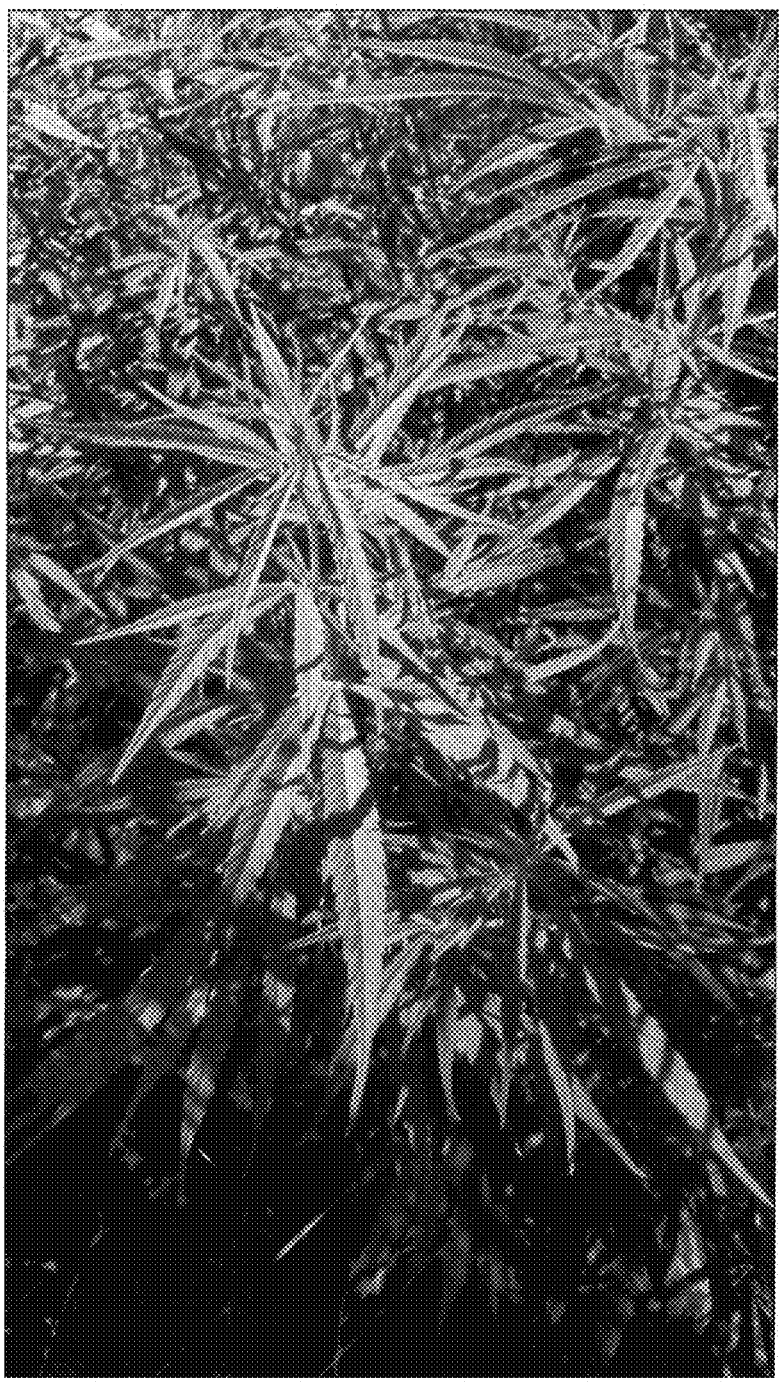
FIG. 3 shows a close-up of the leaves of 'UNIQUE FLOWER ORIGINAL HAZE'.
Figure 4:
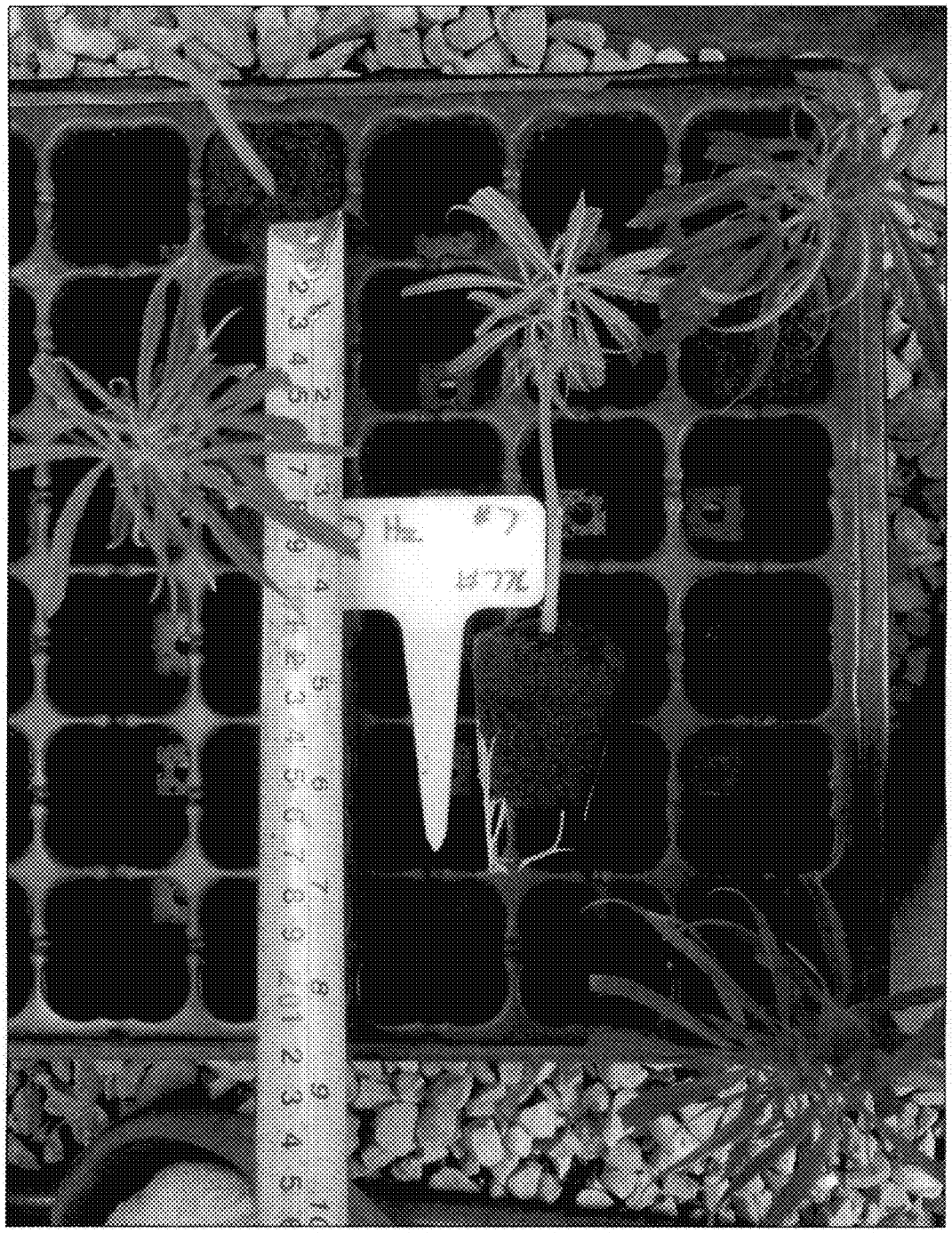
FIG. 4 shows whole plant clones of 'UNIQUE FLOWER ORIGINAL HAZE', including clone #776 from mother plant #7 ('UNIQUE FLOWER ORIGINAL HAZE') at 2 weeks after cutting.
Figure 5:
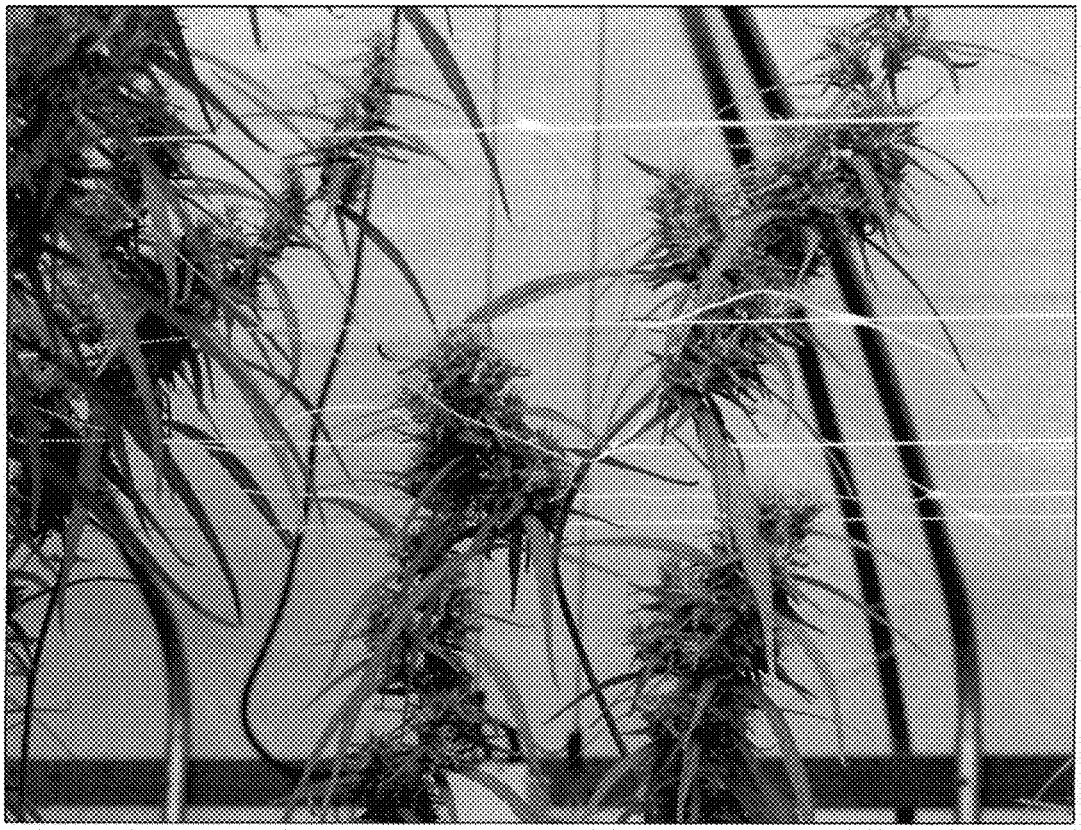
FIG. 5 shows whole plant clones of 'UNIQUE FLOWER ORIGINAL HAZE' a few weeks after cutting.
Figure 6:
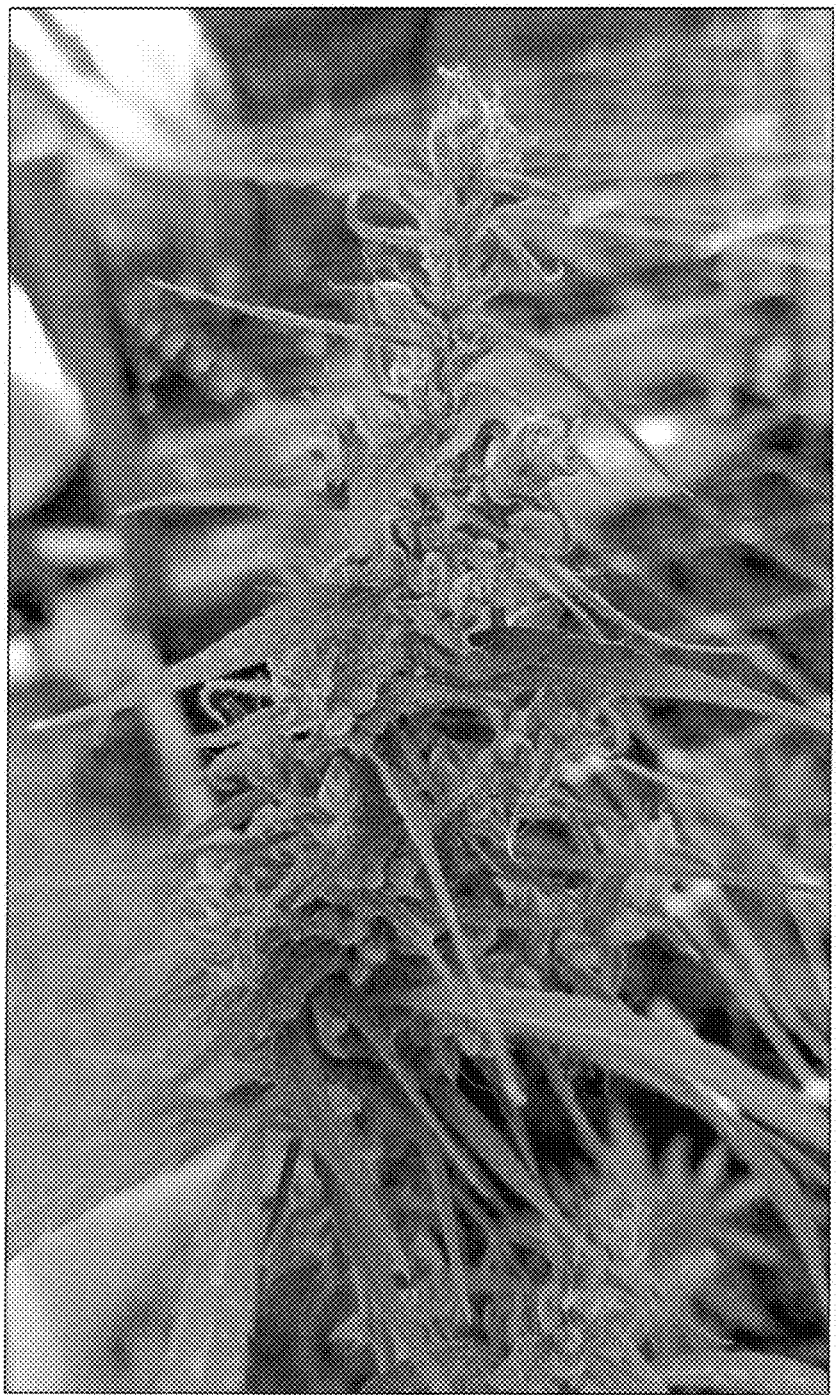
FIG. 6 shows a close-up view of a relatively young inflorescence of a clone of 'UNIQUE FLOWER ORIGINAL HAZE' at 15 weeks after flower initiation.
Figure 7:
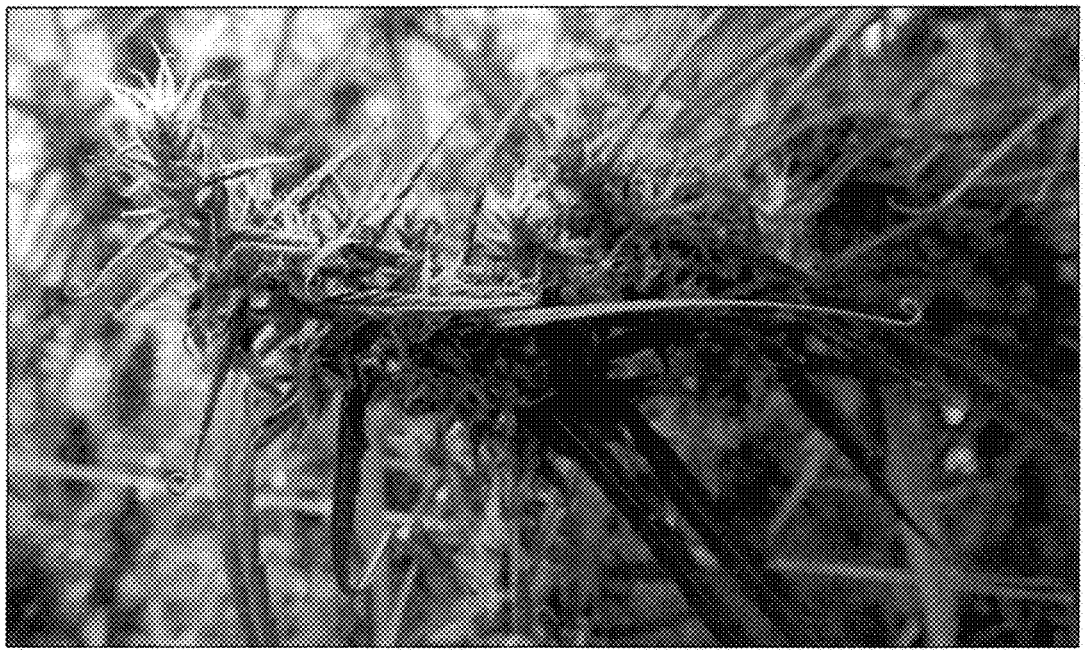
FIG. 7 shows a close-up view of a relatively mature inflorescence of a clone of 'UNIQUE FLOWER ORIGINAL HAZE' at 15 weeks after flower initiation.
Figure 8:
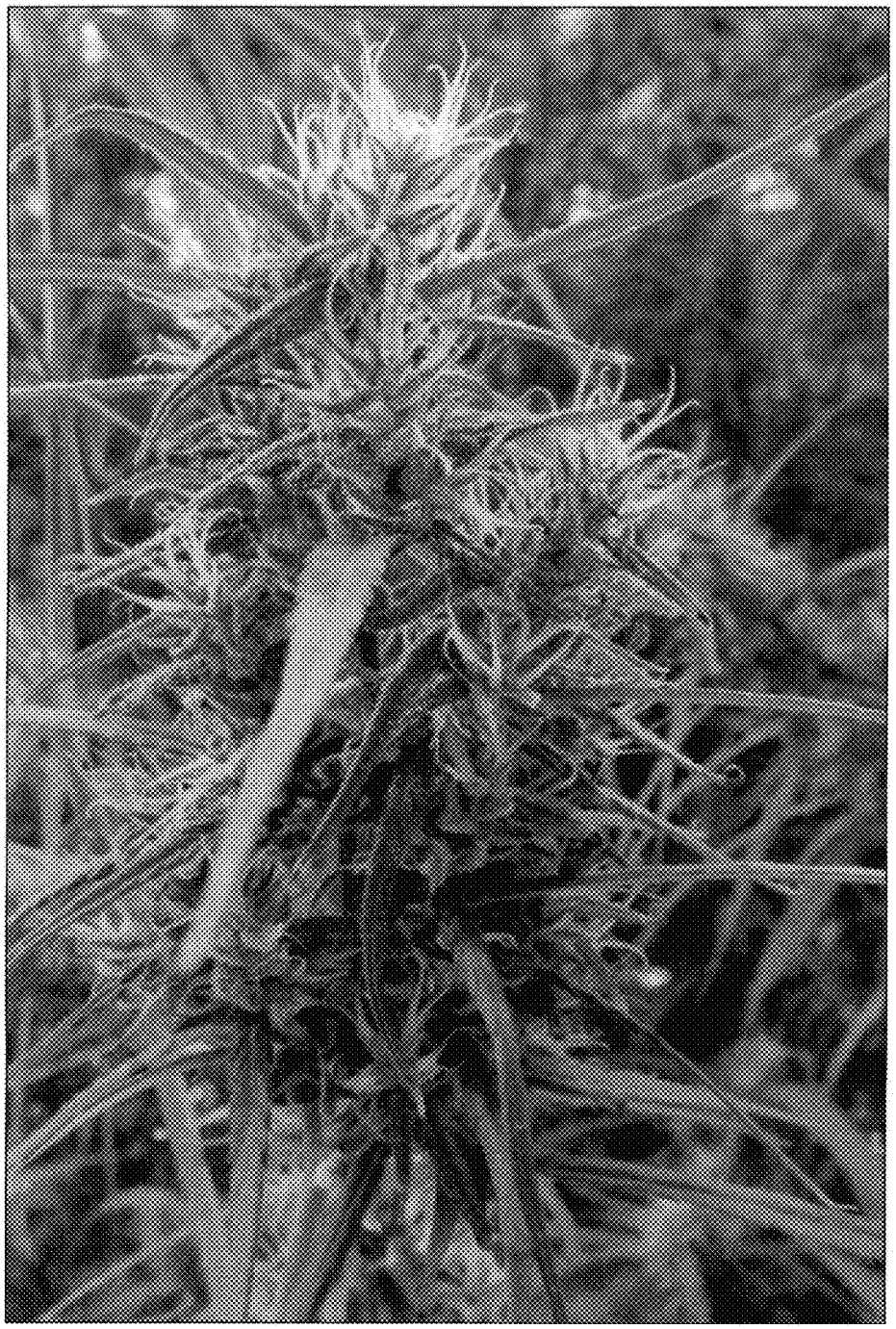
FIG. 8 shows a close-up view of another relatively mature inflorescence of a clone of 'UNIQUE FLOWER ORIGINAL HAZE' at 15 weeks after flower initiation.
Figure 9:
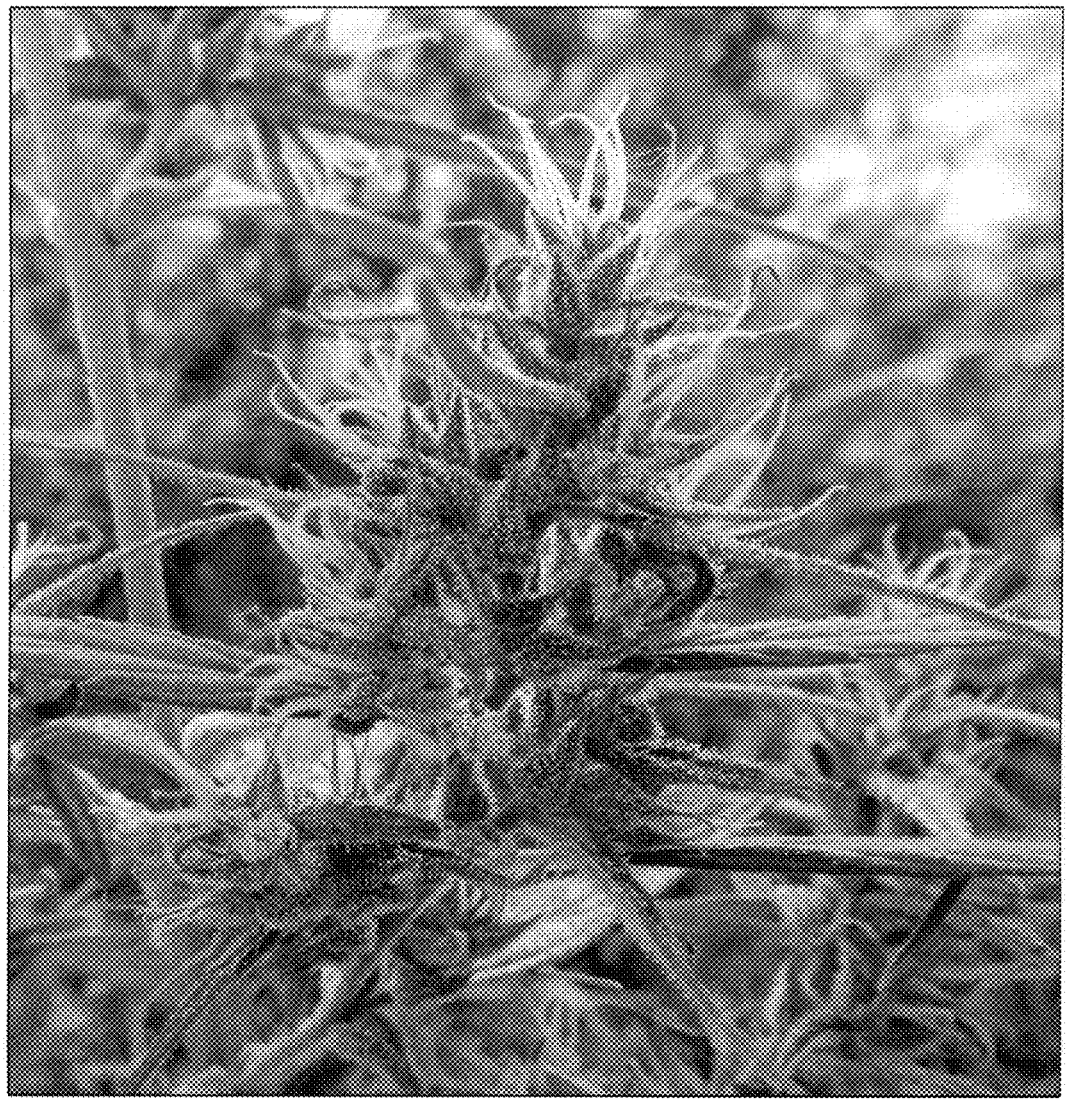
FIG. 9 shows a more close-up view of an inflorescence of a clone of 'UNIQUE FLOWER ORIGINAL HAZE' at 15 weeks after flower initiation, showing dense trichomes.
Figure 10:
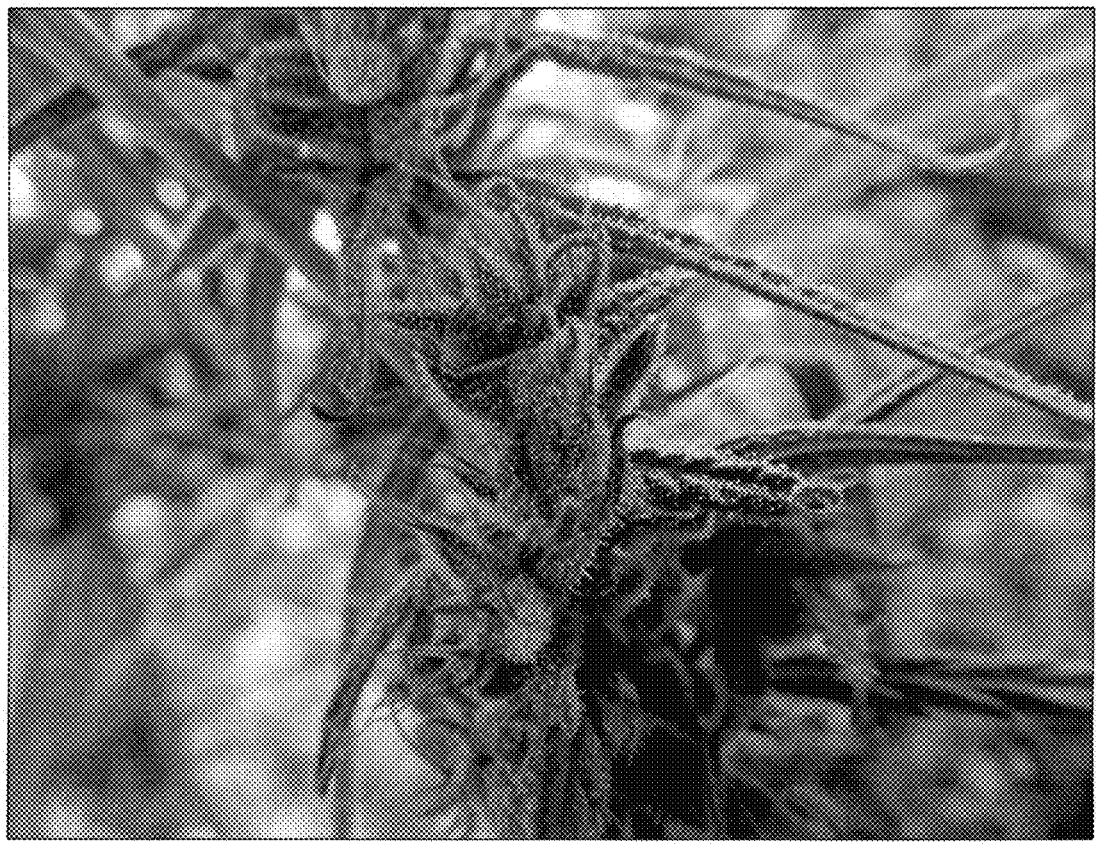
FIG. 10 shows a more close-up view of another inflorescence of a clone of 'UNIQUE FLOWER ORIGINAL HAZE' at 15 weeks after flower initiation, showing dense trichomes.

Tables 2 and 3(a), shown below, provide detailed information on the concentrations of cannabinoids and terpenes, respectively, present in the inflorescences of asexual clones of 'UNIQUE FLOWER ORIGINAL HAZE' grown and harvested in Rainier, Oreg.

Measurements of cannabinoid analytes for 'UNIQUE FLOWER ORIGINAL HAZE' are listed in Table 2, below, based on random sampling from 111.2 g of material from four clones. Sampling and testing was performed and certified by Confident *Cannabis,* 5691 SE International Way, Portland, Oreg. (www.confidentcannabis.com) using CH SOP 4400 methods. Total THC (Calculated Decarboxylated Potential), determined as (THCa*0.877+d9 THC), was 17.38%. Total CBD (Calculated Decarboxylated Potential), determined as (CBDa*0.877+CDB), was 0.10%. For each analyte in Table 2, the limit of quantification (LOQ) was 0.5 mg/g, and an entry "<LOQ" indicates a measurement below this limit of quantification.

TABLE 2

Cannabinoids

| Analyte | Mass CY | Mass (mgt) |
|---|---|---|
| THCa | 17.77 | 177.7 |
| $\Delta_9$-THC | 1.79 | 17.9 |
| THCV | <LOQ | <LOQ |
| CBDa | 0.12 | 1.2 |
| CBD | <LOQ | <LOQ |
| CBDV | <LOQ | <LOQ |
| CBN | <LOQ | <LOQ |
| CBGa | 1.20 | 12.0 |
| CBG | 0.06 | 0.6 |
| CBC | 0.08 | 0.8 |
| Total | 21.01 | 210.1 |

Measurements of terpene analytes for 'UNIQUE FLOWER ORIGINAL HAZE' are listed in Tables 3(a) and 3(b), below, based on random sampling from 111.2 g of material from four clones. Sampling and testing was performed and certified by Confident *Cannabis,* 5691 SE International Way, Portland, Oreg. (www.confidentcannabis.com) using GC-FID CH SOP 401 methods. For each analyte in Tables 3(a) and 3(b), the limit of quantification (LOQ) was 0.02%.

TABLE 3(a)

| Terpenes Detected | | |
|---|---|---|
| Analyte | Mass (%) | Mass (mg/g) |
| β-Myrcene | 0.84 | 8.4 |
| Ocimene 2 | 0.51 | 5.1 |
| cis-B-Farnesene | 0.26 | 2.6 |
| β-Caryophyllene | 0.20 | 2.0 |
| α-Pinene | 0.12 | 1.2 |
| α-Humulene | 0.09 | .9 |
| Linalool | 0.06 | .6 |
| trans-Phytol | 0.05 | .5 |
| Limonene | 0.04 | .4 |
| Terpinolene | 0.03 | .3 |
| (−)-β-Pinene | 0.03 | .3 |

As indicated in Table 3(a), 'UNIQUE FLOWER ORIGINAL HAZE' has 0.84% β-Myrcene. Myrcene has been shown to have anti-neuropathic pain effects, and to cause intracellular calcium influxes by acting on nociceptive Transient Receptor Potential V1 receptors (Jansen, C., et al., Channels, 13:1, 344-366 (2019); www.tandfonline.com/doi/full/10.1080/19336950.2019.1654347). In this way, Myrcene may help facilitate the interaction of Anandamide (AEA)—known as the "Bliss molecule" because it helps to modulate brain reward circuitry—with TRPV1 (Scherma, M., et al., Acta Pharmacologica Sinica, 40:309-323 (2019); www.ncbi.nlm.nih.gov/pmc/articles/PMC6460372/). Myrcene also reduces inflammation by inhibiting IL-1β induced responses such as iNOS production (Rufino, A. T., et al., European J. Pharm., 750:141-150 (2015), rihuc.huc.min-saude.pt/bitstream/10400.4/1789/1/alexandrina%202015.pdf).

As indicated in Table 3(a), 'UNIQUE FLOWER ORIGINAL HAZE' has 0.51% Ocimene 2, also known as β-Ocimene, and 0.26% cis-β-Farnesene. β-Ocimene is produced by both flowers and vegetative plant tissues, and may attract enemies of phytophagous insects, thereby reducing herbivory (Farré-Armengol, G., et al., Molecules 22:1148 (2017); www.ncbi.nlm.nih.gov/pmc/articles/PMC6152128/). β-Ocimene may also induce pest resistance, for example, resistance to aphids (Cascone, P., et al., J. Plant Physiology, 173:28-32 (2015); www.sciencedirect.com/science/article/abs/pii/S0176161714002296?via%3Dihub). In addition, both β-Ocimene and cis-β-Farnesene have acetylcholinesterase (AChE) inhibitory activity (Wojtunik-Kulesza, K. A., et al., Open Chem, 15:332-343 (2017); www.degruyter.com/document/doi/10.1515/chem-2017-0040/html). AChE is an enzyme that breaks down acetylcholine, a neurotransmitter, so these terpenes may support nerve function.

As indicated in Table 3(a), 'UNIQUE FLOWER ORIGINAL HAZE' has 0.20% betaCaryophyllene (BCP) and 0.06% linalool. β-Caryophyllene (BCP) binds directly to CB2 receptors and is a known anti-inflammatory agent with potential for treatment of neurogenic pain. (Johnson, S. A., et al., Hindawi, Article ID 8035301 (2020); www.hindawi.com/journals/ecam/2020/8035301/). Linalool is known to have anxiolytic and antidepressant-like effects. (S. Koyama, et al., Int. J. Mol. Sci., 21:1558 (2020); pubmed.ncbi.nlm.nih.gov/32106479/; Guzmán-Gutiérrez, S. L., et al., Life Sciences, 128:24-29 (2015); www.sciencedirect.com/science/article/abs/pii/S0024320515001381). Linalool is the primary constituent of lavender essential oil, which also contains BCP, and lavender oil has been shown to inhibit fatty acid amide hydrolase (FAAH). (Johnson, 2020.) FAAH is known to hydrolyze AEA, and such inactivation of FAAH may modulate the endocannabinoid system fostering analgesic, anti-inflammatory, anxiolytic and antidepressant effects (Ahn, K., et al., Expert Opin. Drug. Discov. 4(7):763-784 (2009); pubmed.ncbi.nlm.nih.gov/20544003/; Griebel, G., et al., Scientific Reports, 8:2416 (2018); pubmed.ncbi.nlm.nih.gov/29403000/).

As indicated in Table 3(a), 'UNIQUE FLOWER ORIGINAL HAZE' has 0.12% α-Pinene and 0.03% (−)-β-Pinene. It is known that α-pinene protects against inflammation and neuronal damage. (Salehi, B, et al., Biomolecules, 9:738 (2019); www.ncbi.nlm.nih.gov/pmc/articles/PMC6920849/.) Furthermore, α-pinene has been shown to increase the response of gamma-aminobutyric-acid (GABA) receptors, allowing nerve cells to better send and receive chemical messages (Yang, H., et al., Mol Pharmacol, 90:530-539 (2016); pubmed.ncbi.nlm.nih.gov/27573669/). Beta-Pinene has been shown to have antidepressant effects and interacts with dopamine receptors in the brain (Guzmán-Gutiérrez 2015).

As indicated in Table 3(a), 'UNIQUE FLOWER ORIGINAL HAZE' has 0.09% α-humulene and 0.04% limonene. Alpha-humulene has marked anti-inflammatory properties on the airway's allergic inflammation and is known to reduce eosinophil influx into lung tissue (Rogerio, A. P., et al., Btritish J. Pharmacology, 158:1074-87 (2009); www.ncbi.nlm.nih.gov/pmc/articles/PMC2785529/). Limonene has been shown to prevent bronchial obstruction and reduce peribronchial inflammatory cell infiltration when inhaled (Hirota, R., et al., Inhalation Toxicology, 24(6):373-381 (2012); www.si.mahidol.ac.th/th/department//admin/news_files/30_17_1.pdf).

It is also notable that numerous other terpenes were not present in 'UNIQUE FLOWER ORIGINAL HAZE'. For each analyte identified in Table 2(b), any measurement of the analyte in 'UNIQUE FLOWER ORIGINAL HAZE' was below the limit of quantification.

TABLE 3(b)

| Terpenes Not Detected at LOQ = 0.02% | | |
|---|---|---|
| Analyte | Analyte | Analyte |
| Cis-Phytol | α-Terpineol | Nerol |
| Valencene | Cedrol | Borneol |
| Sabinene | Citral | Hexahydro Thymol |
| Ocimene 1 | (−)-Guaiol | Squalene |
| Geraniol | Neryl Acetate | δ-3-Carene |
| Neral | γ-Terpinene | Eucalyptol |
| α-Terpinene | Anisole | Eugenol |
| Caryophyllene Oxide | Fenchone | (−)-Isopulegol |
| Camphor | Isoborneol | Pulegone |
| (−)-α-Bisabolol | Camphene | Cis-Nerolidol |
| α-Cedrene | α-Phellandrene | β-Farnesene |
| Endo-Fenchyl Alcohol | γ-Terpineol | cis-β-Farnesene |
| p-isopropyltoluene | Geranyl Acetate | α-Famesene |
| Azulene | Sabinene Hydrate | |

DETAILED BOTANICAL DESCRIPTION

The following is a detailed botanical description of the new cultivar described herein, designated 'UNIQUE FLOWER ORIGINAL HAZE'. The following description is for plants that were approximately 15 weeks post-initiation of flowering at the time of the measurements, and that were grown in an indoor facility and in a field plot at Rainier, Oreg. 'UNIQUE FLOWER ORIGINAL HAZE' has not been observed under all possible environmental conditions, and phenotypic differences may be observed with variations in environment without any variance in genotype. The color indications provided herein are based on Munsell book of color, available at munsell.com/.

The plant:

*Type* (*life form and habit*).—A vigorous herbaceous, dioecious, tap-rooted annual plant.

*Classification.*—*Cannabis sativa*, ssp. *sativa.*

*Origin*.—Progeny of crosses between Highland Columbian Gold, Punto Rojo, and Santa Marta Columbian Gold.

*Propagation*.—The strain is asexually propagated by stem cutting and cloning.

*Mature habit*.—Extensive fibrous root system with upright and much branched aerial portion of plant having Christmas-tree-like (cone) shape. The growth form of all cloned individuals (n>200) was highly manipulated by systematic removal of terminal buds, inducing a greater branching habit. Overall size in this form varies from 1.6-1.9 m tall and 0.3-0.4 m across at their widest point.

Foliage:

*Leaf arrangement*.—Alternate.

*Form*.—Palmately compound/linear-lanceolate leaflets, 5-11 cm. During peak vegetative growth plant will express up to 11 palmately compound leaflets. During flowering leaflet number decreases to singular linear-lanceolate leaflets.

*Leaf size* (*with petiole*).—8-20 cm long; middle (largest) leaflet 12-14 cm long, 1 cm wide.

*Leaf margin*.—Dentate, coarsely serrated, and the teeth point towards the tip.

*Leaf color*.—Upper side — 7.5GY 6/10; Lower side — 7.5GY 9/12.

*Veins*.—Obliquely continuous throughout leaflet; 7.5Y 9/10.

*Petiole*.—2.5-3 cm long; 5GY 8/8.

*Stipules*.—Acute-bulbous. 1 cm long, 10GY 6/10.

*Aroma*.—Very strong; smells of fresh/sharp vegetable and herbs, pepper, grains of paradise.

Stem:

*Shape*.—Hollow, punctuate, minutely glandular, ribbed with ribs running parallel to stem.

*Size*.—3.5-6 cm diameter at base.

*Color*.—5GY 8/8 striped with 7.5R 4/14 segments in late flower.

*Internode length*.—3-12 cm.

*Breaking action*.—Extremely flexible, resistant to breakage.

Inflorescence:

*Blooming/flowering habit*.—Cymes from 0.5-2.2 m in length. Elongated compound cymes or panicles, forming spikes from 0.3-0.5 m in length, loosely packed with individual small pistillate flowers subtended by small leaves, these with densely packed capitate glandular trichomes.

*Number of flowers*.—50-150 per cyme.

Flowers:

*Shape*.—Calcarate-urceolate; a small green bract enclosing the ovary with two long, slender stigmas projecting well above the bract. Open floral structure with stacked bracts along stems that form flowers in fox tail formations.

*Flower* (*individual pistillate*) *length*.—7 mm.

*Bract*.—Urceolate, 0.3-0.5 cm, 10GY 6/10.

*Stigma*.—Linear-lanceolate, 5-7 mm, 5GY 9/6 while immature, 10R 5/12 when mature.

*Trichome*.— Capitate sessile trichomes (color: clear when immature at day 40 in flowering) are present on the leaves of plants, as well as being noticed in the flowers; During later flowering (day 98 to day 112 in flowering), capitate stalked trichomes (color: N9 at peek maturity) are present. Bulbous and non-glandular trichomes (color: N9) are also present and most noticeable on the petioles.

*Cola* (*terminal bud*).—Elliptical, 10GY 6/10.

*Pedicel*.—Absent.

*Pollen*.—Absent.

*Petal*.—Apetalous; this part is fused and appressed to the base of the ovary with the calyx and the perianth in the *Cannabis* flowers.

*Petal arrangement*.—Free.

General characteristics:

*Time to first flowering*.—4-6 weeks.

*Flowering/blooming period*.—14-16 weeks.

*Flowering stimulus*.—Decreasing light to less than 12 hours per day.

*Hardiness*.—Hardy to 35° F. ambient temperature.

*Rooting rate after cutting/cloning*.—99% vigorous.

*Pest susceptibility*.—Resistant to pests including spider mites, hemp russet mites, aphids, and white flies.

*Disease susceptibility*.—Resistant to diseases such as bud rot or grey mold (*Botrytis cinerea*), *Fusarium* wilt (*Fusarium oxysporum*).

*Storage life*.—Long: 3-8 months with minor changes in physical appearance and/or smell/taste; potentially years if stored in airtight container in a dark and cool location.

*Productivity of flower*.—Approximately 0.23-0.9 kg can be produced per plant, depending on finished plant size (1.0-4.0 m); approximately 400-800 grams can be produced per plant at an average size of 1.3 m×0.7 m.

*Market use*.—Medicinal and recreational.

We claim:

1. A new and distinct *Cannabis sativa* plant named 'UNIQUE FLOWER ORIGINAL HAZE', substantially as described and illustrated herein.

* * * * *